US006723883B1

(12) United States Patent
Therre et al.

(10) Patent No.: US 6,723,883 B1
(45) Date of Patent: Apr. 20, 2004

(54) CONTINUOUS METHOD FOR PRODUCTION OF CINNAMALDEHYDE AND DIHYDROCINNAMALDEHYDE DERIVATIVES

(75) Inventors: Jörg Therre, Worms (DE); Andreas Kramer, Bad Dürkheim (DE); Andreas Weiper-Idelmann, Waldsee (DE); Michael Schulik, Ludwigshafen (DE); Regina Benfer, Altrip (DE); Jürgen Schossig, Fussgönheim (DE); Mathias Haake, Mannheim (DE); Hans-Georg Göbbel, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 39 days.

(21) Appl. No.: 10/110,532
(22) PCT Filed: Oct. 10, 2000
(86) PCT No.: PCT/EP00/09918
§ 371 (c)(1),
(2), (4) Date: Apr. 15, 2002
(87) PCT Pub. No.: WO01/27061
PCT Pub. Date: Apr. 19, 2001

(30) Foreign Application Priority Data

Oct. 14, 1999 (DE) .......................................... 199 49 672

(51) Int. Cl.[7] ................................................ C07C 45/73
(52) U.S. Cl. ....................................... 568/433; 568/434
(58) Field of Search .................................. 568/433, 434

(56) References Cited

U.S. PATENT DOCUMENTS 2,529,186 A * 11/1950 Richmond
3,280,192 A * 10/1966 Levy et al.
3,935,274 A * 1/1976 Jacobsen et al.

* cited by examiner

*Primary Examiner*—Shailendra Kumar
*Assistant Examiner*—Sikarl A. Witherspoon
(74) *Attorney, Agent, or Firm*—Keil & Weinkauf

(57) ABSTRACT

The present invention relates to a continuous process for the preparation of cinnamaldehyde or cinnamaldehyde derivatives by continuous reaction of benzaldehyde derivatives with alkanals in the presence of bases and optionally subsequent continuous hydrogenation in a circulation reactor in the presence of a suspension catalyst and hydrogen to give dihydrocinnamaldehyde derivatives.

21 Claims, 2 Drawing Sheets

Figure 1:
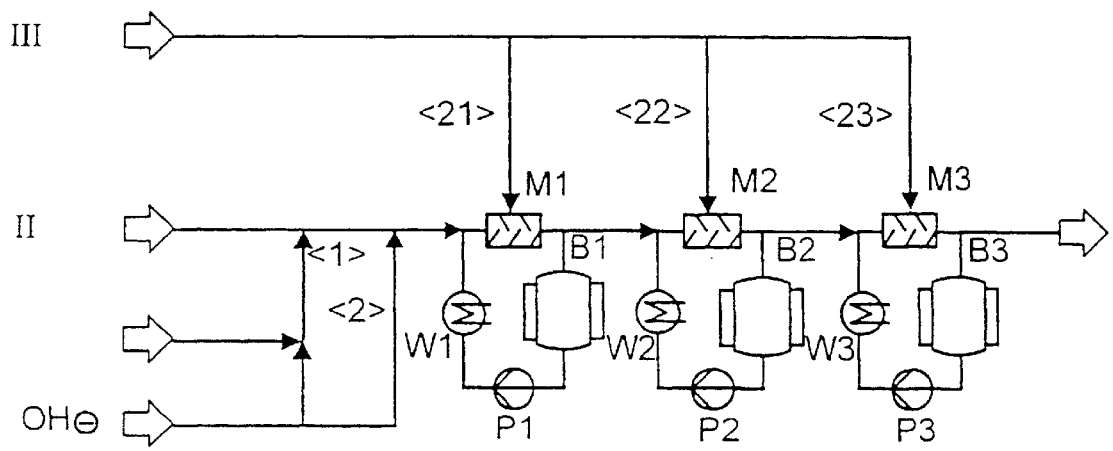

CONTINUOUS METHOD FOR PRODUCTION OF CINNAMALDEHYDE AND DIHYDROCINNAMALDEHYDE DERIVATIVES

The present invention relates to a continuous process for the preparation of cinnamaldehyde or cinnamaldehyde derivatives by continuous reaction of benzaldehyde derivatives with alkanals in the presence of bases and optionally subsequent continuous hydrogenation in a circulation reactor in the presence of a suspension catalyst and hydrogen to give dihydrocinnamaldehyde derivatives.

Cinnamaldehyde derivatives, such as, for example, 2-pentyl-3-phenyl-2-propenal or 2-hexyl-3-phenyl-2-propenal, cinnamaldehyde itself, or the corresponding dihydro compounds, for example cyclamenaldehyde (2-methyl-3-(p-isopropylphenyl)-propanal) or lysmeral (2-methyl-3-(p-tert-butylphenyl)propanal) are used as intermediates for fragrances, or as fragrances themselves and, moreover, are used as starting materials for the synthesis of active ingredients in the pharmaceuticals and crop protection sector (cf. GB 1 086 447).

It is known that cinnamaldehyde derivatives can be prepared by reacting benzaldehyde derivatives with alkanals in the presence of basic catalysts, i.e. by aldol condensation (cf. Houben-Weyl, "Methoden der organischen Chemie" [Methods in Organic Chemistry] volume 7/1, p. 76 et seq. (1954), and U.S. Pat. No. 2,976,321). According to the known prior art, the reactants are reacted in batchwise or semicontinuous processes.

For example, U.S. Pat. No. 2,529,186 from 1947 describes a semicontinuous process for the preparation of cinnamaldehyde by reacting benzaldehyde with ethanal, in which the benzaldehyde, in the presence of, for example, aqueous alkali metal hydroxide, is initially introduced, and the ethanal is slowly added thereto in a slight excess. Here, the alkali metal hydroxide should be used in an amount of from 2.5 to 6.5 parts by weight per part by weight of aldehyde. As is shown by examples, only yields of from 75 to 85% are obtained for this process. Disadvantages of this process are the yields, which are unsatisfactory for use on an industrial scale, and also the requisite large amount of alkali metal hydroxide which, apart from the necessary costs therefor, signifies severe contamination of waste water, and the relatively long reaction time which means that the reaction vessels must be correspondingly large.

D.P. B 9977 from 1950 describes a semicontinuous process for the preparation of cinnamaldehyde by the condensation of benzaldehyde and acetaldehyde by means of alkali in an aqueous medium. In the process, the benzaldehyde should be used in excess and the acetaldehyde should only be added gradually. In addition, per part by weight of benzaldehyde, about 2 to 3 parts by weight of water should be used. Particularly because of the large amount of water which is used, and which has to be purified and disposed of, the process is not economical.

EP 392 579 describes a process for the preparation of α-substituted cinnamaldehydes by reacting benzaldehyde with alkanals. The catalyst used is alkali metal hydroxide, and the solvent used is glycol. Other ancillaries which are used are nonpolar hydrocarbons, such as hexane. It is stated therein (cf. page 2, lines 10–16 and 38–39) that, due to the formation of secondary components which are difficult to remove, the use of reactors through which there is continuous flow is unfavorable. This prejudice has been refuted by our work. In fact, we have surprisingly found that by connecting a plurality of reactors one behind the other and feeding the alkanal into more than one of the reactors, it is possible to prepare, in a relatively simple manner, a cinnamaldehyde derivative whose content of by-products is low, in very good yields.

As well as a semicontinuous procedure, EP 392 579 describes how the process is carried out in a stirred tank reactor through which there is continuous flow and which has a residence time of 9.5 hours. A multistage reactor cascade is not mentioned. Disadvantages of the process described are the long residence time required and the large and expensive reaction vessels which are required as a result. In addition, since the reaction takes place in a system of two liquid, immiscible phases, scale-up from laboratory experiments to an industrial plant is very difficult. Furthermore, regulation of the stirred tank reactor through which there is continuous flow and the exact observance of the correct phase ratio is extremely difficult (computerized control is necessary).

A further disadvantage is the complicated work-up of the reaction mixture, in which the reaction mixture comprising glycol must be extracted repeatedly with hexane. Because of the disadvantages described, the process cannot be carried out economically.

In order to overcome the disadvantages of the process according to EP 392 579, European patent specification EP 771 780 proposes a process for the preparation of α-alkylcinnamaldehyde by reacting benzaldehyde with alkanal with pyrrolidine as basic catalyst. As additional cocatalysts, it recommends acids, such as sulfuric acid or hydrochloric acid. For work-up, the crude reaction product should first be washed with an aqueous sodium hydroxide solution and then neutralized with acid.

A disadvantage of this process is the use of an expensive catalyst, which is added in large amounts and which cannot be recycled. This signifies increased costs for feed materials and disposal. A further disadvantage is the expensive, complicated work-up, in which the reaction product has to be washed with large amounts of hydroxide solution. This operation in turn leads to high feed material costs and disposal costs. Since acids are used as cocatalysts, the apparatuses have to be made from corrosion-resistant materials. The abovementioned disadvantages render the process uneconomical.

The known processes for the preparation of cinnamaldehyde derivatives of the formula II are batchwise or semicontinuous processes which have the disadvantages which stem from this procedure: long reaction times, large reaction apparatuses and batchwise operation which, in the case of use on an industrial scale, results in increased expenditure in terms of personnel and maintenance staff. For processes where the possibility of a continuous operation is mentioned, there is no information on carrying out the reaction, or only individual stirred tank reactors through which there is continuous flow are mentioned, which are unsuitable for the economic preparation of cinnamaldehyde derivatives on an industrial scale for the reasons given above.

The hydrogenation of cinnamaldehyde and derivatives thereof has likewise already been extensively documented in the literature. A review of this is given in the Houben-weyl work, Methoden der organischen Chemie [Methods of Organic Chemistry], 4th edition, 1979, volume 4/1c, page 161 f. and the same work volume 7/1, page 388 ff.

It is known from U.S. Pat. No. 3,280,192 that cinnamaldehyde derivatives, such as dehydrolysmeral (2-methy-3-(p-tert-butylphenyl)propenal) can be transformed to give the dihydro compounds by reaction over palladium-containing catalysts in the presence of hydrogen. The authors give the addition of an aqueous phase which is immiscible with the feed material and has a pH between 8 and 13 as being particularly advantageous for the selectivity of the hydrogenation. Good yields and selectivities are achieved in this batch process.

An improvement in the space-time yield is achieved in DE 26 136 45 if the hydrogenation is carried out at higher temperatures of from 100 to 160° C. compared with the above US application, with repeated exchange of the hydrogen atmosphere.

JP 72 50096 likewise recommends the addition of basic compounds such as $K_2CO_3$ in a batch process for the hydrogenation of cinnamaldehyde derivatives over palladium catalysts. In this process, the starting material is used without solvent in a high purity of >97%.

EP 058 326 also describes a batch process for the reaction of a cinnamaldehyde derivative prepared beforehand in situ over palladium catalysts in the presence of amines.

A continuous reaction procedure for the hydrogenation is described in U.S. Pat. No. 3,520,934, which describes the addition of potassium acetate to palladium on $Al_2O_3$ as catalyst as particularly advantageous.

In U.S. Pat. No. 3,520,935, the use of a particular lithium-containing catalyst is required for carrying out the reaction continuously in order to achieve good space-time yields coupled with high conversions and selectivities. Details relating to the service life of the catalyst, which has to be used in the form of extrudates or spheres in the reactor, are not given.

Overall, the examples for the hydrogenation of cinnamaldehyde derivatives listed in the prior art either require a complex batchwise reaction procedure, with long reaction times and large reaction apparatuses, or, for a continuous reaction procedure on a fixed bed, they require the use of specially prepared catalysts which can only be exchanged in a complex manner when a loss of activity arises, which generally results in the plant being switched off.

In addition, all of the processes described in the prior art start from isolated and purified product. A continuous process which combines the continuous preparation of cinnamaldehyde derivatives starting from the corresponding benzaldehydes and alkanals with a subsequent continuous hydrogenation to give dihydrocinnamaldehyde derivatives is not described in the prior art.

It is therefore an object of the present invention to develop a continuous process for the preparation of cinnamaldehyde or cinnamaldehyde derivatives starting from the corresponding benzaldehydes and alkanals, in which the abovementioned disadvantages of the known processes can be avoided, and also a continuous process for the preparation of dihydrocinnamaldehyde derivatives.

We have found that this object is achieved according to the invention by a process for the (a) continuous preparation of cinnamaldehyde derivatives of the formula I

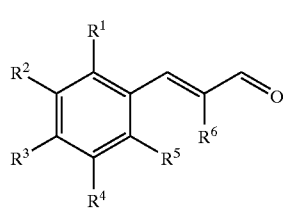

(I), in which $R^1$, $R^2$, $R^3$, $R^4$, $R^5$ and $R^6$, independently of one another, may be hydrogen, $C_1$- to $C_9$-alkyl groups or $C_1$–$C_9$-alkoxy groups, preferably of cinnamaldehyde derivatives of the formula I in which $R^1$, $R^2$, $R^3$ and $R^6$, independently of one another, are hydrogen or $C_1$–$C_9$-alkyl groups and $R^4$ and $R^5$ are hydrogen, by reaction of benzaldehyde derivatives of the formula II

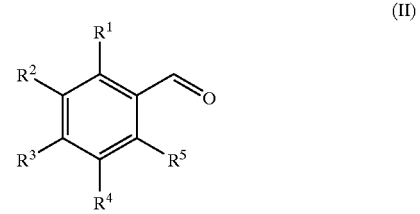

(II)

with alkanals of the formula III

(III)

in the presence of bases, which comprises reacting the reactants continuously in a plant consisting of a plurality of reactors in a cascade system, and introducing the alkanal into more than one of the reactors of the plant and (b) optionally a directly subsequent continuous hydrogenation in a circulation reactor in the presence of a suspension catalyst and hydrogen to give dihydrocinnamaldehyde derivatives of the formula IV,

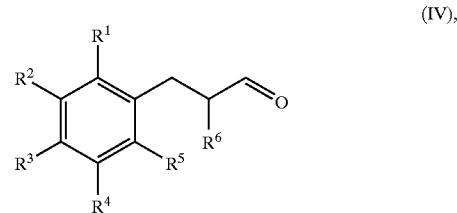

(IV), where $R^1$ to $R^6$ have the meanings given above.

The invention provides both the continuous preparation of the cinnamaldehyde derivative of the formula I and also the preparation of the dihydrocinnamaldehyde derivative of the formula IV by combining process steps (a) and (b).

Preferably, the preparation of the cinnamaldehyde derivatives of the formula I is followed by a hydrogenation to give the corresponding dihydrocinnamaldehyde derivatives of the formula IV.

If stage (a) is followed by a hydrogenation as in (b) the process is distinguished from the prior art firstly by the continuous reaction procedure of both processes and secondly by the fact that purification or isolation of the starting material, which is prepared in the upstream aldol condensation between the benzaldehyde derivative of the formula II and the alkanal of the formula III, is not required for the hydrogenation.

The reaction discharge obtained under (a), following adjustment of a pH to between 7 and 13, preferably between 8 and 9, is passed to the hydrogenation without work-up.

Suitable agents for adjusting the pH are Bröstedt acids, preferably organic acids, such as formic acid, propionic acid, citric acid, phthalic acid, particularly preferably acetic acid.

The benzaldehyde derivatives of the formula II used according to the invention are, for example, benzaldehyde itself, m-isopropyl-benzaldehyde, p-isopropylbenzaldehyde, p-tert-butylbenzaldehyde, m-tert-butylbenzaldehyde, m-methylbenzaldehyde, p-methylbenzaldehyde, o-methylbenzaldehyde, m-anisaldehyde or p-anisaldehyde, or else mixtures of two or more of these benzaldehyde derivatives.

Alkanals of the formula IV suitable for the reaction according to the invention which may be mentioned are, in particular, acetaldehyde, propanal, n- and isobutanal, n- and isopentanal, n- and isohexanal.

Preferred dihydrocinnamaldehyde derivatives of the formula IV are cyclamenaldehyde or lysmeral. Particularly preferably, the process according to the invention (stage (a) and stage (b)) is used to prepare lysmeral.

The catalysts used for the preparation of the cinnamaldehyde derivatives of the formula I (stage (a)) for the process according to the invention are basic compounds, such as the alkali metal hydroxides NaOH, KOH and LiOH, alkaline earth metal hydroxides, and mixtures thereof, or else compounds of the alkali metal and alkaline earth metals which can liberate the corresponding hydroxides in the presence of water, and also ammonia, amines or alkoxides, such as, for example sodium methoxide or potassium tert-butoxide. Aqueous solutions of the alkali metal oxides and hydroxides are particularly advantageous, in particular solutions of sodium oxide or hydroxide, where the concentration of the oxide or of the hydroxide is between 0.5 and 50% by weight, preferably between 10 and 50% by weight. All of the base is generally introduced into the first reactor, but it can also be divided between all of the reactors. The amount of base required is very little, which represents a particular advantage of the process according to the invention. For example, the concentration of the base in the reaction mixture should only be between 0.01% by weight and 20% by weight, preferably between 0.1% by weight and 5% by weight.

Stage (a) of the process according to the invention is illustrated in examples 1 to 4 using a cascade consisting of 3 reactors.

The preferred plant for the novel continuous preparation of the cinnamaldehyde derivatives of the formula I consists, in principle, of a plurality of reactors connected one behind the other in a cascade system. The number of reactors used is generally between 2 and 20, preferably between 2 and 10 and in particular between 2 and 5 reactors. The reactors are operated in a cascade system, which means that the outflow from one reactor is in each case passed to the next reactor. The reaction mixture formed is then discharged at the exit of the last reactor.

In a less preferred configuration of the process, the product mixture can also be drawn off from one or more of the downstream reactors and returned to one or more of the upstream reactors.

Suitable reactors are non-back-mixed reactors, such as tubular reactors or delay time containers provided with internals, but preferably back-mixed reactors, such as stirred tank reactors, loop reactors, jet loop reactors or jet reactors. It is, however, also possible to use combinations of successive back-mixed reactors and non-back-mixed reactors.

If appropriate, it is also possible for a plurality of reactors to be combined in a multistage apparatus. Such reactors are, for example, loop reactors with built-in perforated plates, cascaded containers, tubular reactors having intermediate-feed capability, or stirred columns. It is advisable to equip all or some of the individual reactors with heat exchangers. In the reactors, thorough mixing of the reactants must be ensured, which can be achieved, for example, by stirring or recirculating, optionally in combination with treatment using static mixers or mixing nozzles.

The volume of the reactors is adjusted so that the average residence time of the reaction mixture in the reactors is between 5 minutes and 8 hours, in particular between 10 minutes and 5 hours. It is particularly advantageous to use reactors which have approximately the same volume, although in principle it is also possible to use reactors which have varying volumes.

The temperature in the reactors is generally between 20 and 130° C., in particular between 30 and 100° C.

The pressure in the reactors is unimportant, although it should be sufficiently high for the contents of the reactors to remain almost liquid. Generally, pressures of from 1 bar to 40 bar are required for this purpose, and the pressure is advantageously between 1 and 6 bar.

The benzaldehyde or the benzaldehyde derivative of the formula II is preferably introduced into the first reactor of the plant with a cascade system. In some cases, however, it may also be necessary to add fractions of the benzaldehyde (derivative) to the other reactors of the plant with a cascade system.

In a particularly preferred embodiment of the process according to the invention, the benzaldehyde or the benzaldehyde derivative is premixed with the fraction of the alkanal which is added to the same reactor prior to being introduced into the reactors. For this premixing, it is possible to use the customary mixing apparatuses, such as static mixers, stirred tank reactors, mixing nozzles or the like. The premixing of the two reactants leads to an increase in selectivity. This selectivity increase is particularly surprising since the patent specification U.S. Pat. No. 2,529,186 states that a premixing of the reactants would reduce the selectivity.

The alkanal should be added to more than one reactor of the reaction plant. It is particularly advantageous to add some of the alkanal to each reactor of the plant in a cascade system. Furthermore, it has, however, also been found that uniform distribution of the alkanal between all of the reactors is unfavorable for high selectivity. It has therefore been found to be advantageous to introduce between about 20% and 70% of the total amount of alkanal to be added, in particular between 40 and 60% of the alkanal, into the first reactor, and to add the remaining amount, i.e. from about 80 to 30% of alkanal, to the other reactor(s). Furthermore, it is particularly advantageous to introduce at least some of the alkanal into the reactor in premixed form with some or all of the benzaldehyde derivative.

The alkanal is generally used in liquid form. In principle, however, a gaseous addition is also possible.

In a particularly preferred embodiment of the process, the amount of alkanal is chosen such that the molar ratio of benzaldehyde (derivative) to alkanal in all of the reactors is between 5 and 100 mol/mol, preferably between 10 and 60 mol/mol. This molar ratio can be readily determined by analysis of the reaction mixture by means of known analytic methods, for example by gas chromatography. Generally, a single analysis per day suffices, but in particular cases it may also be necessary to use online analysis.

The conversion of the benzaldehyde (derivative) is between 20% and 95%, preferably between 30 and 80%, depending on the temperature, the residence time and the amount of base. A particular advantage of the process according to the invention is that conversion of the alkanal is sufficiently high for recovery of the unreacted alkanal to generally be dispensed with.

To increase the selectivity, solvents can be added to the reaction mixture. Suitable solvents are alcohols, such as methanol, ethanol, propanol, isopropanol, butanol or ethylene glycols and also ethers, such as diethyl ether or cyclic ethers, such as dioxane. A particularly advantageous solvent is methanol. The solvent can be introduced into the individual reactors on its own or admixed with one or more of the reactants or the base. However, preference is given to adding all of the solvent to the first reactor.

The product from the reaction plant can be readily worked up by means of the customary separation operations, such as crystallization, phase separation or fractional distillation, and the cinnamaldehyde derivative can thus be isolated in a simple manner. It is generally advantageous, prior to working up the reaction mixture, to at least partially neutralize the basic catalyst by adding inorganic or organic acids.

Using the process according to the invention (stage (a)) it is possible to prepare cinnamaldehyde and, generally, cinnamaldehyde derivatives of the formula I in high purity and very good quality in a simple manner. The process according to the invention requires only a few, simple, small and cost-effective apparatuses. With the help of the process according to the invention it is possible to prepare the cinnamaldehyde derivatives of the formula I in high selectivities, based both on the alkanal and on the benzaldehyde derivative.

If stage (a) is followed by a hydrogenation according to stage (b) to give the dihydrocinnamaldehyde derivative, then said hydrogenation is carried out in a reactor as in U.S. Pat. No. 5,939,589, in which the liquid phase and the gas phase is passed through a device with orifices or channels with a hydraulic diameter of from 0.5 to 20 mm, preferably 1 to 10 mm, particularly preferably 1 to 3 mm. The hydraulic diameter is the quotient of 4× the cross section of the orifice and the circumference thereof.

The device with orifices or channels for conveying the reaction medium can consist of a bed, a knit, an open-cellular foam structure, preferably made of plastic (e.g. polyurethane or melamine resins) or ceramic, or a packing element, as is already known in principle, i.e. in terms of its geometric shape, from distillation and extraction technology.

Such packing elements, which offer the advantage of a low pressure loss, are, for example, wire mesh packings. For the purposes of the present invention, however, the packings fundamentally have a significantly, usually by a factor of from 2 to 10, smaller hydraulic diameter than comparable internals in the field of distillation and extraction technology.

Instead of fabric packings, it is also possible to use packings made of other woven, knitted or felted liquid-permeable materials. Further suitable packings are sheet-metal packings. Also advantageous are packings made of expanded metal, such as, for example, packings of the Montz BSH type. The orifices, e.g. perforations, must be kept correspondingly small. A decisive feature for the suitability of a packing for the purposes of the present invention is not its geometry, but the orifice sizes or channel widths which arise for conveyance within the packing.

During the hydrogenation, commercially available catalyst particles with an average particle size of from 0.0001 to 2 mm, preferably from 0.001 to 0.1 mm, particularly preferably from 0.005 to 0.05 mm, can be used for the suspension.

The hydrogenation is carried out by the process according to the invention in a reactor with one of the above-described internals in the presence of hydrogen at a pressure between 1 and 100 bar, preferably 1 and 30 bar, particularly preferably 1 and 15 bar. The reaction temperatures are between 10 and 160° C., preferably between 20 and 80° C., particularly preferably between 40 and 75° C.

Internals which can be used in the hydrogenation reactor are fabric packings or sheet-metal packings. Reaction mixture, catalyst and hydrogen are pumped through the reactor in a circuit at high speed. The superficial velocity of gas phase and liquid phase is here more than 50 $m^3/m^2h$, preferably in the range from 50 to 300 $m^3/m^2h$, particularly preferably between 100 to 250 $m^3/m^2h$. The gas phase is thoroughly mixed with the liquid phase by means of an injector nozzle.

For the hydrogenation, a commercially available suspension catalyst is used which preferably contains at least palladium as active component. As well as palladium, the catalyst may also comprise further active components, such as, for example, zinc, cadmium, platinum, silver or a rare earth metal. The catalyst can be used in metallic and/or oxidic form inter alia on support materials. Suitable support materials are, for example, $SiO_2$, $TiO_2$, $ZrO_2$, $Al_2O_3$ or carbon, such as graphite, carbon black or activated carbon, particular preference being given to activated carbon. The content of palladium is between 0.1 and 10% by weight, preferably between 1 and 7% by weight.

The hydrogenation according to the invention for the preparation of dihydrocinnamaldehyde derivatives is characterized by the fact that the liquid is passed through the above-described device with orifices and channels at a superficial velocity of about 50 to 300 $m^3/m^2h$, preferably from 250 to 200 $m^3/m^2h$. If the gas phase is present at the same time, its superficial velocity is preferably 50 to 300 $m^3/m^2h$, particularly preferably 100 to 200 $m^3/m^2h$.

The present hydrogenation can be carried out in various continuously operated reactor constructions, such as jet tube reactors, bubble columns or tube-bundle reactors. However, the internals mentioned above preferably do not necessarily fill the entire reactor. The reactor according to the invention is preferably a vertically arranged bubble column through which, in the presence of a gas phase, the flow is preferably in cocurrent from bottom to top. Another preferred reactor is a heatable and coolable tube-bundle reactor in which the internals according to the invention are accommodated in the individual tubes. In the presence of a gas phase, the flow through the reactor is preferably in cocurrent from bottom to top. The suspneded catalyst material can be introduced and removed again using customary techniques (sedimentation, centrifugation, cake filtration, crossflow filtration).

Figure 3:
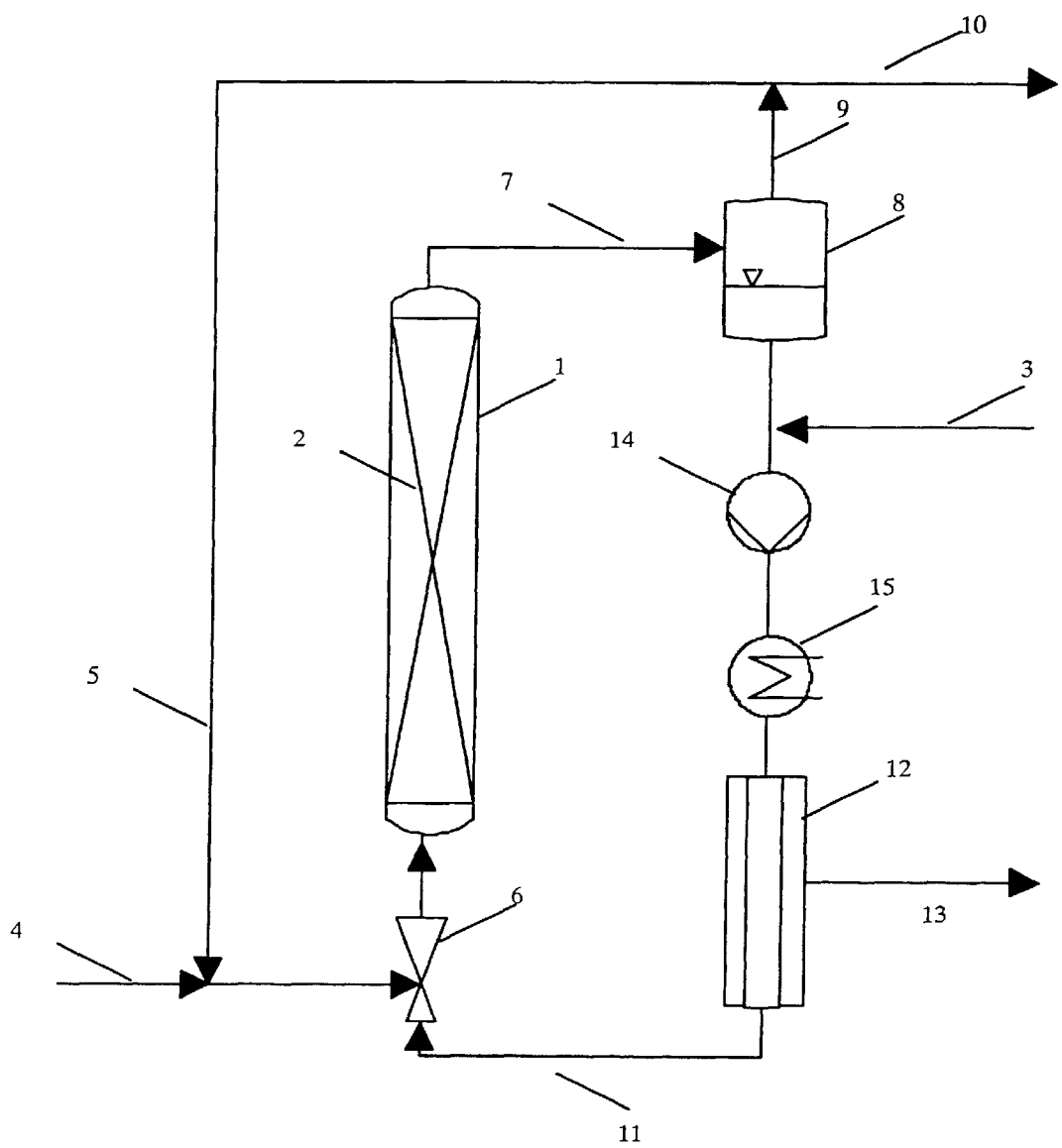

For example, a reactor for the hydrogenation of dehydrolysmeral to lysmeral using a suspension catalyst according to the present invention of stage (b) is described in detail by reference to FIG. 3. By way of example, FIG. 3 shows the experimental set-up of a continuously operating reactor (bubble column) 1 with packing 2, which is fed via lines 3 with liquid and via line 4 with fresh gas. The circulating gas 5 is mixed by means of the mixing nozzle 6 with fresh gas and the suspension 11 circulated by the pump 14. The reactor discharge is passed via line 7 into the separation vessel 8, where the gas phase is separated off and drawn off via line 9. To limit the buildup of gaseous impurities, a partial stream is removed from this amount of gas via line 10, and the remainder is passed to the reactor via line 5. The suspended catalyst remains in the reactor system by being retained via a crossflow filter 12, and only catalyst-free liquid phase emerges via line 13 and is taken off. The temperature in the reactor system can be adjusted in a targeted manner via the heat exchanger 15.

The examples below serve to illustrate the invention in more detail without, however, limiting it thereto:

Aldol Condensation (Process Stage (a))

EXAMPLE 1 (without premixing)

The apparatus (cf. FIG. 1) consisted of three containers B1, B2 and B3 connected in series and each having a volume of 275 ml, each of which was heated via a double-walled jacket using a thermostat and cooled by means of heat exchangers W1, W2 and W3 and whose contents were circulated by pumps P1, P2 and P3. The benzaldehyde derivative was mixed with the solvent and some of the base and added to the first container (stream <1>). The second part of the base was added to the first container (stream <2>). The alkanal was incorporated into the corresponding containers by means of the mixing nozzles M1, M2 and M3 (streams <21>, <22>, <23>).

Metered into the first container were, as stream <1>, 217 ml/h of a mixture consisting of 54% by weight of methanol, 45.5% by weight of p-tert-butylbenzaldehyde and 0.5% of a 50% strength by weight aqueous sodium hydroxide solution, as stream <21>, 13.1 g/h of propanal and, as stream <2>, 6 g/h of sodium hydroxide solution (50% strength in water). Metered into the second container were, as stream <22>, 6.6 g/h of propanal and, into the third container, as stream <23>, 3.3 g/h of propanal. The temperatures of the separately heatable containers were between 47° C. and 48° C. The amount of circulated liquid was fixed at 600 ml/min in each container. After the cascade had been in operation for a period of 8 h, the product from the third container had the following composition: <0.1% by weight of propanal; 21% by weight of p-tert-butylbenzaldehyde, 20.5% by weight of 3-(p-tert-butylphenyl)-2-methyl-2-propenal. This corresponds to a conversion of 48% of the amount of p-tert-butylbenzaldehyde, and the selectivity, based on the benzaldehyde derivative, is 85%, and based on the propanal is 62% of theory.

EXAMPLE 2 (without premixing)

The apparatus described in example 1 was used.

Metered into the first container were, as stream <1>, 217 ml/h of a mixture consisting of 54% by weight of methanol, 45.5% by weight of p-tert-butylbenzaldehyde and 0.5% by weight of a 50% strength by weight aqueous sodium hydroxide solution, as stream <21>, 13.1 g/h of propanal and, as stream <2>, 6 g/h of sodium hydroxide solution (50% strength in water). Metered into the second container were, as stream <22>, 6.6 g/h of propanal and into the third container, as stream <23>, 3.3 g/h of propanal. The temperatures of the separately heatable containers were between 47° C. and 48° C. The amount of circulated liquid was adjusted to 1 200 ml/min in each container. After the cascade had been in operation for a period of 8 h, the product from the third container had the following composition: <0.1% by weight of propanal; 19% by weight of p-tert-butylbenzaldehyde and 23.5% by weight of 3-(p-tert-butylphenyl)-2-methyl-2-propenal. This corresponds to a conversion of p-tert-butylbenzaldehyde of 52%. The selectivity of 3-(p-tert-butylphenyl)-2-methyl-2-propenal was thus 87% of theory, based on the benzaldehyde derivative, and 70% by weight based on the propanal.

EXAMPLE 3 (with premixing of p-tert-butylbenzaldehyde and propanal)

The apparatus (cf. FIG. 2) consisted of three containers B1, B2 and B3 connected in series and each having a volume of 275 ml, each of which was heated via a double-walled jacket using a thermostat and cooled via heat exchangers W1, W2 and W3. The contents of these containers were circulated by pumps P1, P2 and P3. The benzaldehyde derivative and the fraction of the alkanal intended for the first container were premixed in the mixing container M1 and then metered into the first container B1 (stream <1>). The amount of alkanal intended for the second and third containers was incorporated into the corresponding containers by means of mixing nozzles M2 and M3 (streams <22> and <23>). The solvent was mixed with the base, and the resulting mixture was introduced into the first container (stream <2>).

Metered into the first container were, as stream <1>, 114 g/h of a mixture consisting of 87.7% by weight of p-tert-butyl-benzaldehyde and 12.3% by weight of propanal and, as stream <2>, 129.7 g/h of a mixture consisting of 4% by weight of aqueous sodium hydroxide solution (50% strength by weight) and 96% by weight of methanol. Metered into the second container were, as stream <22>, 6.6 g/h of propanal, and metered into the third container, as stream <23>, 4.2 g/h of propanal. The temperatures of the separately heatable containers were between 43° C. and 51° C. The amount of circulated liquid was set at 1 200 ml/min in each container. After the cascade had been in operation for a period of 8 h, the product of the third container had the following composition: <0.1% by weight of propanal, 16.2% by weight of p-tert-butylbenzaldehyde and 28.3% by weight of 3-(p-tert-butylphenyl)-2-methyl-2-propenal. This corresponds to a conversion of p-tert-butylbenzaldehyde of 60% of theory. The selectivity, based on the benzaldehyde derivative, was thus 94% of theory, and 83% of theory based on the propanal.

EXAMPLE 4 (with premixing of p-tert-butylbenzaldehyde and propanal, catalyst sodium methoxide)

Figure 2:
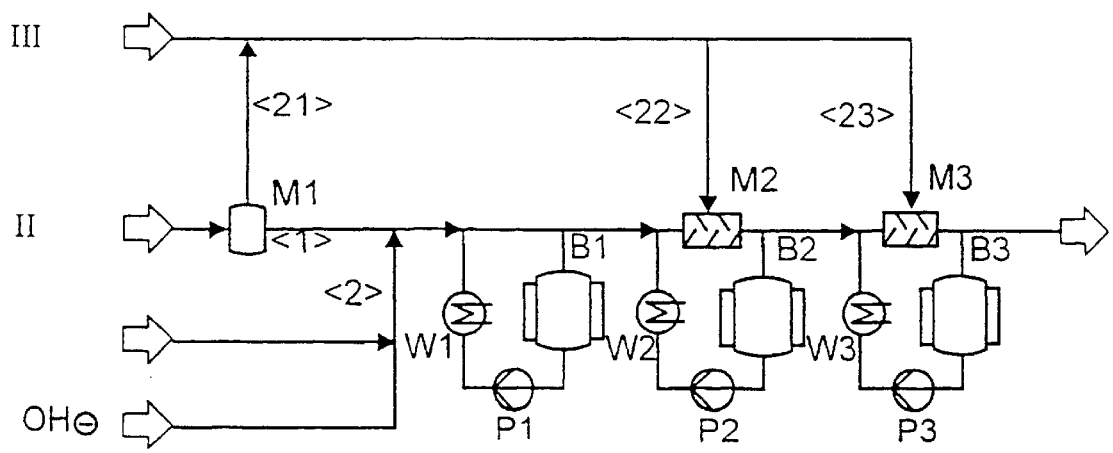

The apparatus described in example 3 and shown diagrammatically in FIG. 2 was used.

Metered into the first container were, as stream <1>, 114 g/h of a mixture consisting of 87.7% by weight of p-tert-butyl-benzaldehyde and 12.3% by weight of propanal and, as stream <2>, 123 g/h of a mixture comprising 1 mol of sodium methoxide per mole of methanol. Metered into the second container were, as stream <22>, 6.6 g/h of propanal and into the third container, as stream <23>, 4.2 g/h of propanal. The temperatures of the separately heatable containers were between 43 and 50° C. The amount of circulated liquid was set at 1 200 ml/min in each container. After the cascade had been in operation for a period of 8 h, the product of the third container had the following composition: <0.1% by weight of propanal, 20.4% by weight of p-tert-butylbenzaldehyde and 20.3% by weight of 3-(p-tert-butyl-phenyl)-2-methyl-2-propenal. This corresponds to a conversion of p-tert-butylbenzaldehyde of 49%. The selectivity of 3-(p-tert-butylphenyl)-2-methyl-2-propenal was thus 83% of theory based on the benzaldehyde derivative and 59% of theory based on the propanal.

EXAMPLE 5 (with premixing of p-tert-butylbenzaldehyde and propanal, catalyst potassium hydroxide solution)

The apparatus described in example 3 and shown diagrammatically in FIG. 2 was used.

Metered into the first container were, as stream <1>, 114 g/h of a mixture consisting of 87.7% by weight of p-tert-butyl-benzaldehyde and 12.3% by weight of propanal and, as stream <2>, 123 g/h of a mixture consisting of 5% by weight of aqueous potassium hydroxide solution (25% strength by weight) and 95% by weight of methanol. Metered into the second container were, as stream <22>, 6.6 g/h of propanal and into the third container, as stream <23>, 4.2 g/h of propanal. The temperatures of the separately heatable containers was between 48 and 51° C. The amount of circulated liquid was set at 1 200 ml/min in each container. After the cascade had been in operation for a period of 24 h, the product of the third container had the following composition: <0.1% by weight of propanal, 16.4% by weight of p-tert-butyl-benzaldehyde and 30.8% by weight of 3-(p-tert-butylphenyl)-2-methyl-2-propenal. This corresponds to a conversion of p-tert-butylbenzaldehyde of 58%. The selectivity of 3-(p-tert-butylphenyl)-2-methyl-2-propenal was thus 99% of theory, based on the benzaldehyde derivative, and 91% of theory based on the propanal.

Hydrogenation (Process Stage (b))

The reaction was used in a bubble column (1000 mm, 27.3 mm diameter) equipped with a fabric packing corresponding to the present invention for the hydrogenation. The experimental set-up corresponded to FIG. 3. The geometry of the packing corresponded to a commercially available fabric packing of the Montz A1 1200 type. The surface per unit volume of the packing is 1 200 m²/m³, this figure only relating to the surface of the fabric. The liquid with the suspended catalyst and the gas were introduced into the reactor from below at a superficial velocity of 200 m³/m²h.

The reaction was carried out continuously under a hydrogen pressure of 10 bar. The catalyst used was a conventional suspension catalyst with a content of 5% palladium on activated carbon which had an average particle size of 30 μm.

EXAMPLE 6

The feed used for the packed bubble column was the product from the continuous aldol condensation of p-tert-butylbenzaldehyde (TBA) with propanal following adjustment to a pH of 8.6 without distillative purification. Such a feed solution usually has the composition 50% by weight of methanol, 29% by weight of dehydrolysmeral (DHL), 13% by weight of TBA, 5% by weight of water, 1% by weight of high-boiling components etc. The temperature was adjusted to 60° C. using thermostats. The conversion was >96% at a selectivity of >93%. The space velocity is 5.8 $kg_{DHL}/(kg_{cat}*h)$, and the space-time yield is 118 $kg_{DHL}/(m^3h)$.

EXAMPLE 7

The feed used for the packed bubble column was a feed as described above (example 6) which was additionally diluted in the ratio 1:2 with product from the hydrogenation. Such a feed solution usually has the composition 50% by weight of methanol, 20% by weight of lysmeral, 10% by weight of dehydrolysmeral, 13% by weight of TBA, 5% by weight of water, 1% by weight of high-boiling components etc. The temperature was adjusted to 60° C. in this case too using thermostats. The amount of feed was 600 g/h. Under these conditions, a conversion of 98.2% and simultaneously a selectivity of 88.4% could be achieved. The space-time yield was 103 $kg_{DHL}/m^3*h$, and the space velocity was 3.7 $kg_{DHL}/(kg_{cat}*h)$

EXAMPLE 8

The feed used for the packed bubble column was a feed as described above (example 6) which was additionally diluted in the ratio 1:2 with product from the hydrogenation. Such a feed solution usually has the composition 50% by weight of methanol, 20% by weight of lysmeral, 10% by weight of dehydrolysmeral, 13% by weight of TBA, 5% by weight of water, 1% by weight of high-boiling components etc. The temperature was adjusted to 60° C. in this case too using thermostats. The amount of feed was 900 g/h. Under these conditions, a conversion of 94.5% and simultaneously a selectivity of 90% could be achieved. The space-time yield was 253 $kg_{DHL}/m^3*h$, and the space velocity was 8.5 $kg_{DHL}/(kg_{cat}*h)$.

We claim:
1. A process for the
   (a) continuous preparation of a cinnamaldehyde compound of formula I

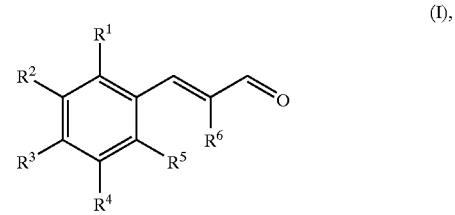

(I), in which
$R^1$, $R^2$, $R^3$, $R^4$, $R^5$ and $R^6$, independently of one another, are hydrogen, $C_1$- to $C_9$-alkyl groups or $C_1$–$C_9$-alkoxy groups, by reacting a benzaldehyde compound of formula II

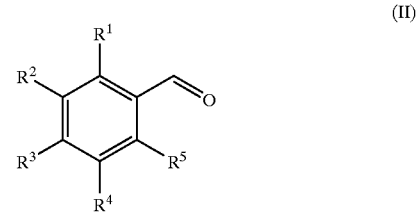

(II)

with an alkanal of formula III

(III)

in the presence of a base, which comprises
reacting the reactants continuously in a plant consisting of a plurality of reactors in a cascade system,
and introducing fractions of the alkanal of formula (III) into more than one of the reactors of the cascade system, and
(b) optionally subsequent continuous hydrogenation in a circulation reactor in the presence of a suspension catalyst and hydrogen to give a dihydrocinnamaldehyde compound of formula IV,

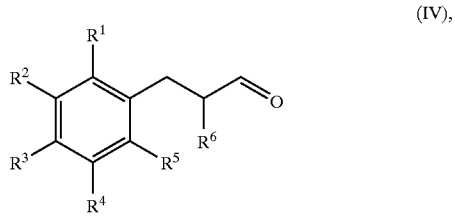

(IV), where $R^1$ to $R^6$ have the meanings given above.
2. A process which comprises
(a) continuous preparation of a cinnamaldehyde compound of formula I

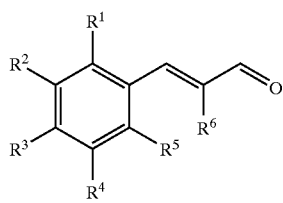

in which
R¹, R², R³, R⁴, R⁵ and R⁶, independently of one another, are hydrogen, $C_1$- to $C_9$-alkyl groups or $C_1$–$C_9$-alkoxy groups, by reacting a benzaldehyde compound of formula II

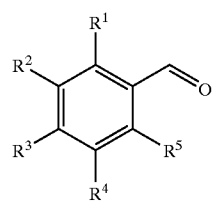

with an alkanal of formula III

in the presence of a base, which comprises
reacting the reactants continuously in a plant consisting of a plurality of reactors in a cascade system,
and introducing fractions of the alkanal of formula (III) into more than one of the reactors of the cascade system, and
(b) subsequent continuous hydrogenation in a circulation reactor in the presence of a suspension catalyst and hydrogen to give a dihydrocinnamaldehyde compound of formula IV,

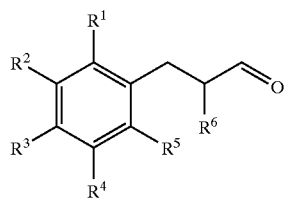

where R¹ to R⁶ have the meanings given above.

3. A process as claimed in claim 1, wherein the benzaldehyde compound of formula II is benzaldehyde itself, m-isopropylbenzaldehyde, p-isopropylbenzaldehyde, p-tert-butylbenzaldehyde, m-tert-butylbenzaldehyde, m-methylbenzaldehyde, p-methylbenzaldehyde, o-methylbenzaldehyde, m-anisaldehyde or p-anisaldehyde, or a mixture of 2 or more of these benzaldehyde compounds.

4. A process as claimed in claim 1, wherein the number of reactors used under (a) in the plant is between 2 and 20.

5. A process as claimed in claim 1, wherein the number of reactors used under (a) in the plant is between 2 and 6.

6. A process as claimed in claim 1, wherein the reactors used under (a) are stirred tank reactors, loop reactors, jet loop reactors, jet reactors or tubular reactors, optionally with recirculation circuit.

7. A process as claimed in claim 1, wherein fractions of the alkanal are introduced into each of the reactors used.

8. A process as claimed in claim 1, wherein between 20% and 70% of the total amount of alkanal added is introduced into the first reactor.

9. A process as claimed in claim 1, wherein the process is carried out such that the conversion of the benzaldehyde compound of formula II is between 20% and 95%.

10. A process as claimed in claim 1, wherein the benzaldehyde compound of formula II introduced into the first reactor is in premixed form in a mixture with a fraction of the alkanal.

11. A process as claimed in claim 1, wherein the molar ratio of the benzaldehyde compound of formula II and the alkanal in the reaction mixture is between 5 mol/mol and 100 mol/mol.

12. A process as claimed in claim 2, wherein the dihydrocinnamaldehyde compound is cyclamenaldehyde or lysmeral.

13. A process as claimed in claim 2, wherein the hydrogenation of the cinnamaldehyde compound of formula II is carried out in a suspension reactor with internals without prior purification of the product obtained in (a).

14. A process as claimed in claim 2, wherein the catalyst particles of the hydrogenation (b) have an average particle size of from 0.0001 to 2 mm.

15. A process as claimed in claim 2, wherein the internals used in the hydrogenation reactor under (b) are fabric packings or sheet-metal packings.

16. A process as claimed in claim 2, wherein the superficial velocity of gas phase and liquid phase is more than 50 $m^3/m^2h$.

17. A process as claimed in claim 2, wherein the reactor used under (b) is a jet reactor, a bubble-column reactor or a tube-bundle reactor.

18. A process as claimed in claim 2, wherein the suspension catalyst under (b) comprises at least palladium as active component.

19. A process as claimed in claim 18, wherein the proportion of palladium is 0.1 to 10% by weight.

20. A process as claimed in claim 18, wherein the catalyst is used on a support containing $SiO_2$, $TiO_2$, $ZrO_2$, $Al_2O_3$ or carbon.

21. A process as claimed in claim 18, wherein the catalyst is used on a support containing activated carbon.

* * * * *